(12) United States Patent
Subbiah et al.

(10) Patent No.: US 8,280,144 B2
(45) Date of Patent: Oct. 2, 2012

(54) SYSTEM AND METHOD FOR ANALYZING MATERIAL PROPERTIES USING HYPERSPECTRAL IMAGING

(75) Inventors: Jeyamkondan Subbiah, Lincoln, NE (US); Chris Richard Calkins, Lincoln, NE (US); Ashok Samal, Lincoln, NE (US)

(73) Assignee: Goldfinch Solutions, LLC, Lincoln, NE (US)

( * ) Notice: Subject to any disclaimer, the term of this patent is extended or adjusted under 35 U.S.C. 154(b) by 1151 days.

(21) Appl. No.: 12/035,080

(22) Filed: Feb. 21, 2008

(65) Prior Publication Data

US 2008/0199080 A1    Aug. 21, 2008

Related U.S. Application Data

(60) Provisional application No. 60/890,895, filed on Feb. 21, 2007.

(51) Int. Cl.
*G06K 9/00* (2006.01)

(52) U.S. Cl. ........... 382/141; 250/227.11; 250/227.2; 348/488

(58) Field of Classification Search ........... 382/141, 382/190, 110, 284; 356/237.1, 419, 300; 250/339.09, 458.1
See application file for complete search history.

(56) References Cited

U.S. PATENT DOCUMENTS

| | | | |
|---|---|---|---|
| 5,991,028 A * | 11/1999 | Cabib et al. | 356/456 |
| 6,075,891 A * | 6/2000 | Burman | 382/191 |
| 6,198,834 B1 | 3/2001 | Belk et al. | |
| 6,256,409 B1 * | 7/2001 | Wang | 382/170 |
| 6,563,580 B1 * | 5/2003 | Aignel et al. | 356/300 |
| 6,587,575 B1 | 7/2003 | Windham et al. | |
| 6,639,665 B2 | 10/2003 | Poole | |
| 7,190,813 B2 * | 3/2007 | Daley et al. | 382/110 |
| 7,218,775 B2 * | 5/2007 | Kokko et al. | 382/156 |
| 7,263,226 B1 * | 8/2007 | Stein et al. | 382/190 |
| 7,337,065 B2 * | 2/2008 | Adler-Golden et al. | 702/3 |
| 7,450,761 B2 * | 11/2008 | Portigal et al. | 382/191 |

* cited by examiner

*Primary Examiner* — Tarifur Chowdhury
*Assistant Examiner* — Isiaka Akanbi
(74) *Attorney, Agent, or Firm* — Hemingway & Hansen, LLP; Eugenia S. Hansen

(57) ABSTRACT

Systems and methods are provided for analyzing material properties of an object using hyperspectral imaging. An exemplary method includes obtaining a hyperspectral image of an object; analyzing the hyperspectral image according to an algorithm; and correlating data obtained from the analysis with material properties of the object.

16 Claims, 7 Drawing Sheets

SYSTEM AND METHOD FOR ANALYZING MATERIAL PROPERTIES USING HYPERSPECTRAL IMAGING

CROSS-REFERENCE TO RELATED APPLICATIONS

This application claims the benefit of U.S. Provisional Application Ser. No. 60/890,895 filed Feb. 21, 2007.

STATEMENT REGARDING FEDERALLY SPONSORED RESEARCH OR DEVELOPMENT

Not applicable.

BACKGROUND OF THE INVENTION

The U.S. beef industry forms a large part of the nation's food and fiber industry. To facilitate marketing, beef grading standards were developed by the USDA to classify carcasses into quality and yield grades. Beef tenderness is an important quality attribute associated with consumer satisfaction. Presently, the USDA grading system is unable to incorporate a direct measure of tenderness because there is no accurate, rapid, nondestructive method for predicting tenderness available to the beef industry. Thus, beef carcasses are not priced on the basis of actual tenderness, creating a lack of incentives for producers to supply a tender product.

SUMMARY OF THE INVENTION

The present invention is defined by the claims below. But summarily, embodiments provide for using hyperspectral imaging to determine material properties of an object. According to embodiments of the invention, examples of such objects may include, but are not limited to, cuts of beef or other types of meat. According to further embodiments of the invention, examples of such objects may include, but are not limited to, samples of various types of tissue from a human or other animal.

In a first illustrative aspect, a system is provided for using hyperspectral imaging to determine material properties of an object. One embodiment of the system includes an imaging component for obtaining a hyperspectral image of at least a portion of an object; an analysis component for analyzing the hyperspectral image to generate data that describes material properties of the object; and an output component for outputting the data.

In a second illustrative aspect, a method is provided for determining material properties of an object using hyperspectral imaging. One embodiment of the method includes obtaining a hyperspectral image of at least a portion of the object; removing redundant information to create a simplified image by performing at least one of a principal component analysis and a partial least squares analysis; extracting one or more image-textural features from the simplified image; and correlating the image-textural features with material properties of the object.

In a third illustrative aspect, a method is provided for predicting a cooked-beef tenderness grade by analyzing a corresponding fresh cut of beef using hyperspectral imaging. One embodiment of the method includes obtaining hyperspectral image data relating to at least a portion of a cut of beef; selecting a region of interest; reducing the dimensionality of the spectral data by performing at least one of a principal component (PC) analysis and a partial least squares (PLS) analysis over the region of interest; extracting one or more image-textural features by performing at least one of a co-occurrence matrix analysis, a wavelet analysis, and an analysis utilizing Gabor filters; and analyzing the image-textural features to determine a tenderness grade for the cut of beef.

BRIEF DESCRIPTION OF THE SEVERAL VIEWS OF THE DRAWINGS

Illustrative embodiments of the present invention are described in detail below with reference to the attached drawing figures, which are incorporated by reference herein and wherein.

DETAILED DESCRIPTION OF THE INVENTION

Figure 1:
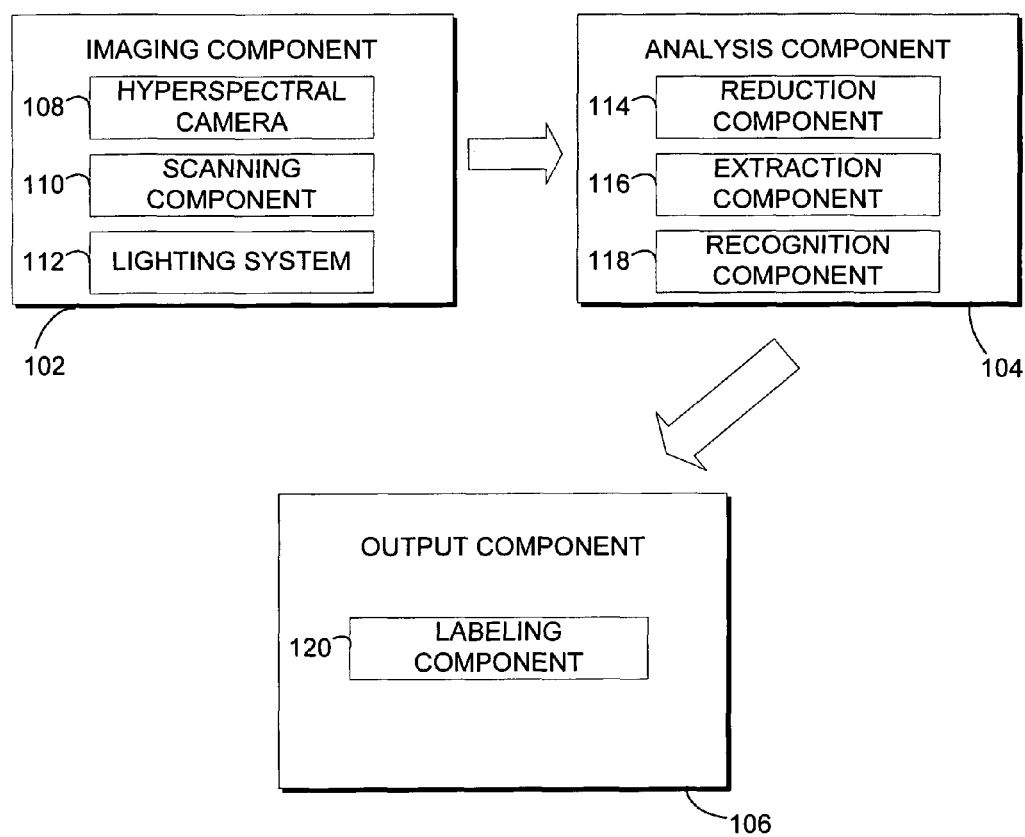
FIG. 1 is a block diagram illustrating an exemplary system for analyzing material properties of an object using hyperspectral imaging according to an embodiment of the present invention.

Tenderness is related to two major components: muscle structure and biochemical activity. Tender beef has fine muscle fibers, whereas tough beef has visibly coarser muscle fibers. Two non-destructive methods for beef tenderness prediction were video image analysis (VIA) and near-infrared (NIR) spectroscopy. VIA has been used to extract color textural features to predict tenderness but is limited in predicting tenderness because biochemical information, such as protein degradation related to aging is not considered. In NIR analysis light reflected from the beef sample in the near-infrared region of the spectrum contains information about biochemical properties of a beef sample. Chemometric models based on the spectral data can be used to predict tenderness categories but they achieve only limited success because muscle structural information is not considered With reference to FIG. 1, an exemplary system 100 for analyzing material properties of an object using hyperspectral imaging according to an embodiment of the present invention is shown. System 100 may include an imaging component 102, an analysis component 104, and an output component 106. System 100 is merely an example of one suitable system and is not intended to suggest any limitation as to the scope of use or functionality of the present invention. Neither should system 100 be interpreted as having any dependency or requirement related to any single component or combination of components illustrated therein.

Imaging component 102 may include a hyperspectral camera 108, a scanning component 110, and a lighting system 112. In one embodiment, the hyperspectral camera 108 may include an optical sensor configured to detect electromagnetic energy that has been reflected off the surface of a sample. As will be readily appreciated by those skilled in the art, any number of various optical sensors may be used to accommodate collecting images in various spectral regions for use in analyzing the properties of a sample object.

For example, in one embodiment, the hyperspectral camera 108 may be configured to collect images in the 200-400 nanometer (nm) wavelength region, which corresponds to ultraviolet light. In another embodiment, the hyperspectral camera 108 may be configured to collect images in the 400-700 nm region, which corresponds to visible light. In other embodiments, the hyperspectral camera 108 may be configured to collect images in the near-infrared regions, which may include, for example, wavelength ranges of 700-1,000 nm, 1000-1,700 nm, and/or 1,700-2,500 nm. In further embodiments, the hyperspectral camera 108 may be configured to collect images in the thermal region, which may correspond to 8,000-12,000 nm. In still further embodiments, the hyperspectral camera 108 may be configured to collect images in any combination of wavelength regions, such as, for example, the regions mentioned above.

The hyperspectral camera 108 may be configured to perform various techniques of imaging, such as imaging techniques useful in producing images in various wavelength ranges such as those discussed above. Such imaging techniques may include spectroscopy techniques such as, for example, reflectance, transmission, scattering, and fluorescence. For example, in one embodiment, the hyperspectral camera 108 may include a sensor having semiconductor material, the sensor being configured to be used in an x-ray transmission imaging. In other embodiments, the hyperspectral camera 108 may include a sensor such as, for example, a photomultiplier tube or an avalanche photodiode detector for use in performing a fluorescence spectroscopy process. In further embodiments, other materials may be used to detect electromagnetic waves of various wavelengths. Any of the sensors according to the embodiments discussed above others not discussed herein, or combinations thereof, may be used to generate hyperspectral images of an object.

In an embodiment, the hyperspectral camera 108 may include a charged-coupled-device (CCD) digital video camera and a spectrograph. The CCD camera may be of any number of different varieties and models such as, for example, the Model IPX-2M30 camera made by Imperx, Inc. The spectrograph may also be of any number of different varieties and models such as, for example, the Enhanced series Imspector V10E, made by Specim.

In an embodiment, scanning component 110 may include a linear slide for moving an object past the hyperspectral camera 108. Any linear slide may be used such as, for example, the linear slide Model: MN10-0300, manufactured by Velmex, Inc. The linear slide may be operated by using a motor. In one embodiment, the motor is a stepper motor such as, for example, the stepper motor Model MDrive 23, manufactured by Intelligent Motion Systems. In one embodiment of the present invention, the scanning component 110 may include a controlling computer for synchronizing the operation of the hyperspectral camera 108 with the operation of the linear slide. In another embodiment, the hyperspectral camera 108 may be mounted on an apparatus that moves the hyperspectral camera 108 past the object. In a further embodiment, the hyperspectral camera 108 may include adjustable mirrors which enable the hyperpectral camera 108 to scan a desired object without moving the hyperspectral camera 108 or the object. In a further embodiment, a scanning rate may be selected and provided by using the controlling computer such that square pixels are achieved.

With continued reference to FIG. 1, the imaging component 102 includes a lighting system 112. In one embodiment, the lighting system 112 includes a concentrated light source for directing electromagnetic energy at an object. The concentrated light source may be configured to direct a particular wavelength of light at an object, after which a hyperspectral camera 108 may detect reflected or transmitted light from the light source. The concentrated light source may include light sources such as, for example, lasers for fluorescence imaging or broad-band light sources such as, for example, tungsten halogen lights.

Figure 7:
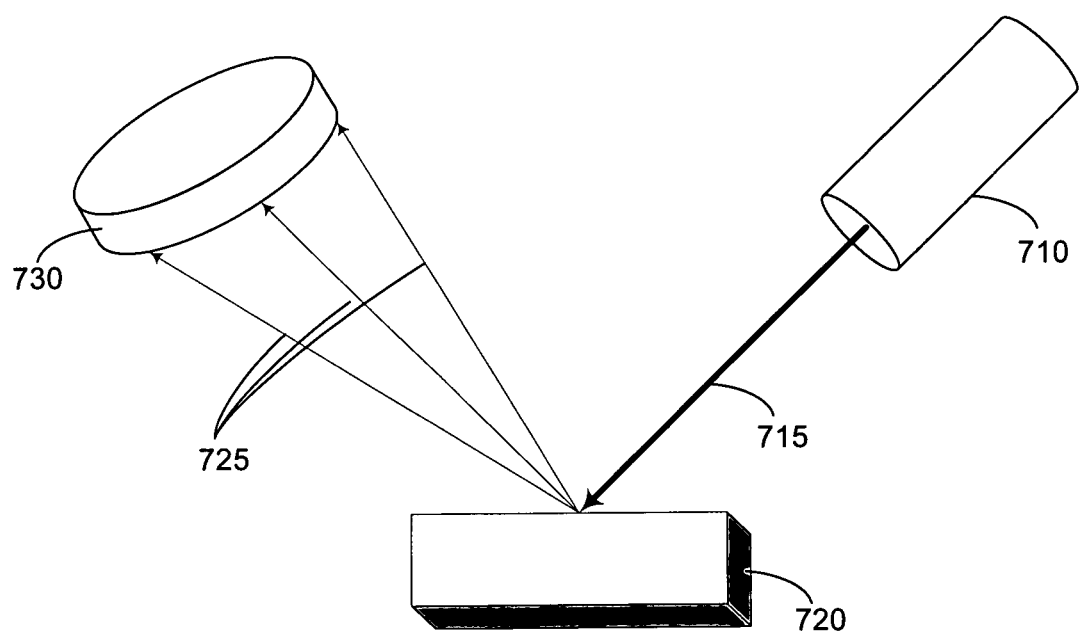
FIG. 7 is a schematic diagram illustrating an exemplary spectroscopy technique according to an embodiment of the present invention.

For example, FIG. 7 shows an illustrative example of a hyperspectral camera and lighting system 700 configured to utilize a concentrated light source 710 in accordance with an embodiment of the present invention. In an embodiment, as shown in FIG. 7, a concentrated light source 710 may direct light 715 at an object 720. The object 720 may alter, for example, the trajectory of the light 715, and the resulting light 725, which may be scattered or transmitted, may be detectable by a sensor 730. In various embodiments, any number of concentrated light sources may be used in such a scattering process.

Figure 4:
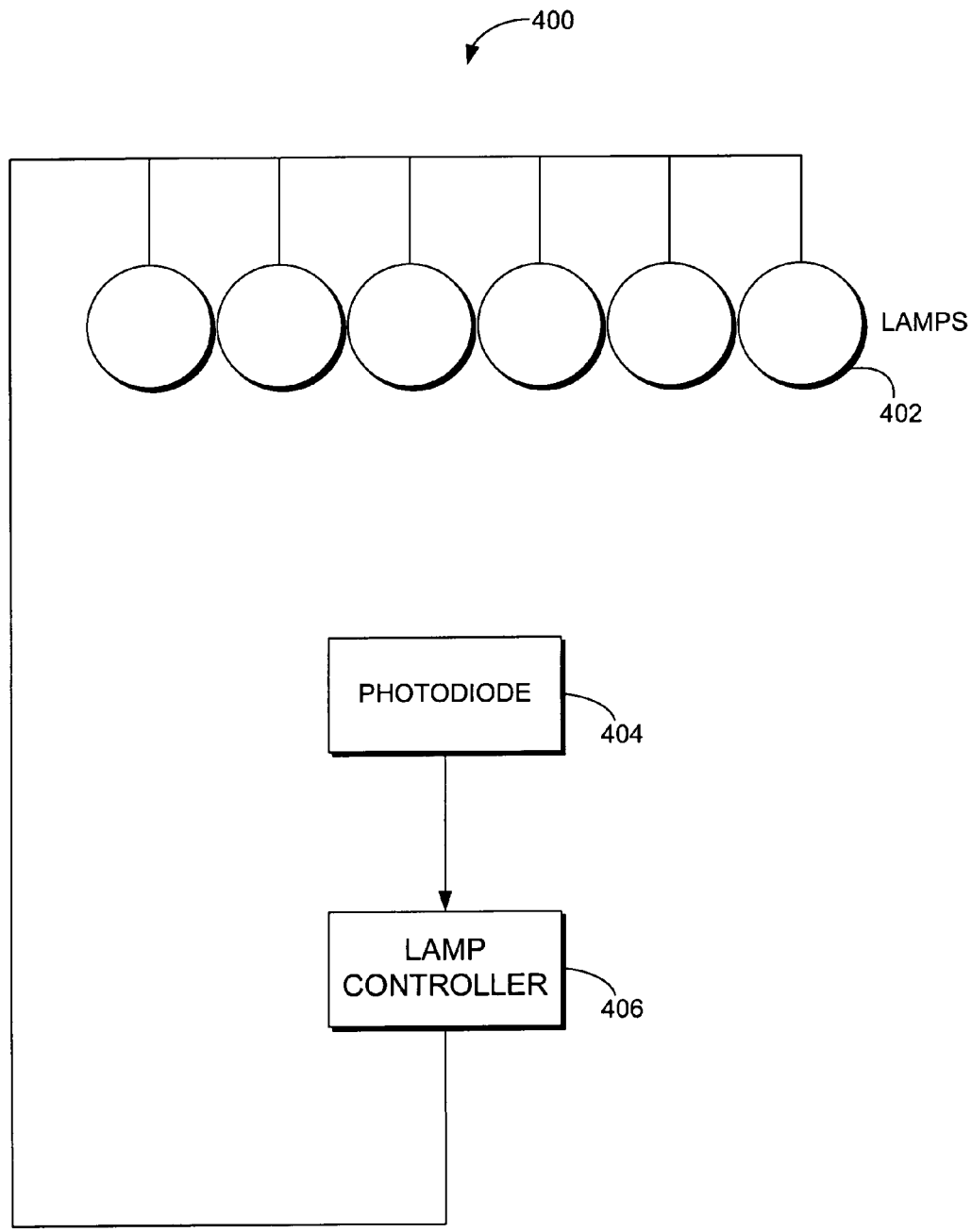
FIG. 4 is a block diagram illustrating an exemplary diffuse lighting system suitable for use in implementing an embodiment of the present invention.

In another embodiment, lighting system 112 may include a diffuse lighting system. An illustration of an exemplary diffuse lighting system according to an embodiment of the present invention is shown in FIG. 4. Turning briefly to FIG. 4, as illustrated therein, diffuse lighting system 400 may comprise a plurality of lamps 402 configured to provide constant intensity output. Additionally, diffuse lighting system 400 may have a hemispherical dome, which may have a viewport, disposed over the lamps. In an embodiment, an inner surface of the dome may be painted with a reflectance coating such as, for example Munsell white reflectance coating, distributed by Edmund Optics.

In various embodiments, the lamps may be of any type known in the art and the system may comprise any number of lamps necessary to achieve a quality lighted environment. In one embodiment, for example, diffuse lighting system may include six 50 W tungsten halogen lamps, as illustrated in FIG. 4. In various embodiments of the present invention, a photodiode 404 may be coupled to a lamp controller 406 in a feedback loop configuration. As will be apparent to those skilled in the art, any number of various types of lamp controllers may be used such as, for example, a lamp controller model TXC300-72/120, manufactured by Mercron Industries. The lamp controller may be used to convert lower frequency AC voltage to high frequency voltage. For example, in one embodiment, a lamp controller may be used to convert 60 Hz AC voltage to 60 kHz voltage.

As those skilled in the art will readily appreciate, some lamps such as tungsten halogen lamps may dim over the course of the lamp's lifetime. Therefore, in one embodiment, the photodiode 404 may provide feedback to the lamp controller 406. Based on the feedback, the current input to the lamps 402 may be increased to provide a constant intensity output.

Returning to FIG. 1, analysis component 104 may comprise mechanisms, computer programs, systems, algorithms etc., for analyzing hyperspectral images to generate data that describes material properties of an object. In one embodiment, analysis component 104 may include a reduction component 114 for reducing the dimensionality of the hyperspectral data contained in a hyperspectral image. In an embodiment, reducing the dimensionality of hyperspectral data may include, for example, removing redundant information such as by performing a principal component (PC) analysis or a partial least squares (PLS) analysis. In an embodiment, the analysis component 104 may include an extraction component 116 for extracting image-textural features from a hyperspectral image. The extraction component 116 may extract image-textural features in any number of ways, for example, by performing a co-occurrence matrix analysis, a wavelet analysis, or an analysis that utilizes Gabor filters. Additionally, in an embodiment, the analysis component 104 may include a recognition component 118 for using pattern recognition algorithms such as, for example, regression, discriminant analysis, neural networks, and fuzzy modeling to relate image-textural features to properties associated with the object.

In an embodiment, output component 106 may include, for example, output devices for storing, transmitting, displaying, or printing data. Such output devices may include, for example, printers, monitors, modems, etc. For example, output component 106 may include a computer monitor for displaying tables and graphs that represent data generated by the analysis component 104. In another embodiment, output component 106 may include a laser printer for printing visual representations or tabulations of such data. In still further embodiments, output component 106 may include a communication device that communicates at least a portion of the data generated by analysis component 104 to an external device or to another component of the system 100. In various embodiments, output component 106 may include one or more databases for storing data generated by the analysis component 104.

Additionally, in an embodiment of the present invention, output component 106 may include a labeling component 120. Labeling component 120 may be operable to attach or apply a label or marking of some kind to an object or to a package in which an object is contained. The label or marking attached or applied by labeling component 120 may provide information relating to at least a portion of the data generated by the analysis component 104. In one embodiment, the system 100 may be located at a meat packing plant, and may mark or label meat products as they are packaged for wholesale. In another embodiment, for example, the system 100 may be located at a retailer, and may be used to mark or label meat products as they are readied for sale. In further embodiments, the system 100 may be located at any desired location, and a labeling component 112 may or may not be utilized as part of the implementation of the present invention.

Figure 2:
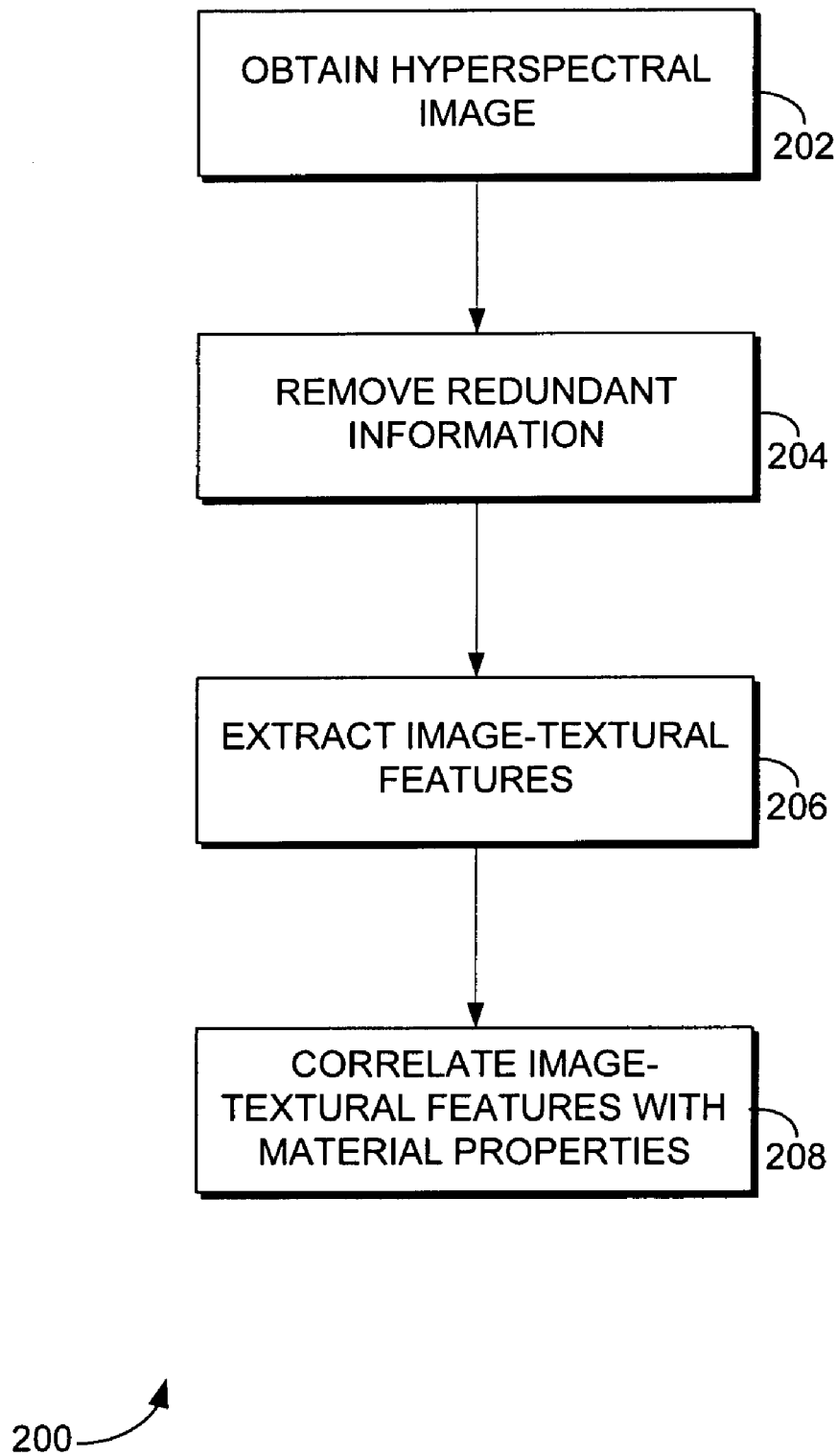
FIG. 2 is a flow diagram illustrating an exemplary method of determining material properties of an object using hyperspectral imaging according to an embodiment of the present invention.
Figure 5:
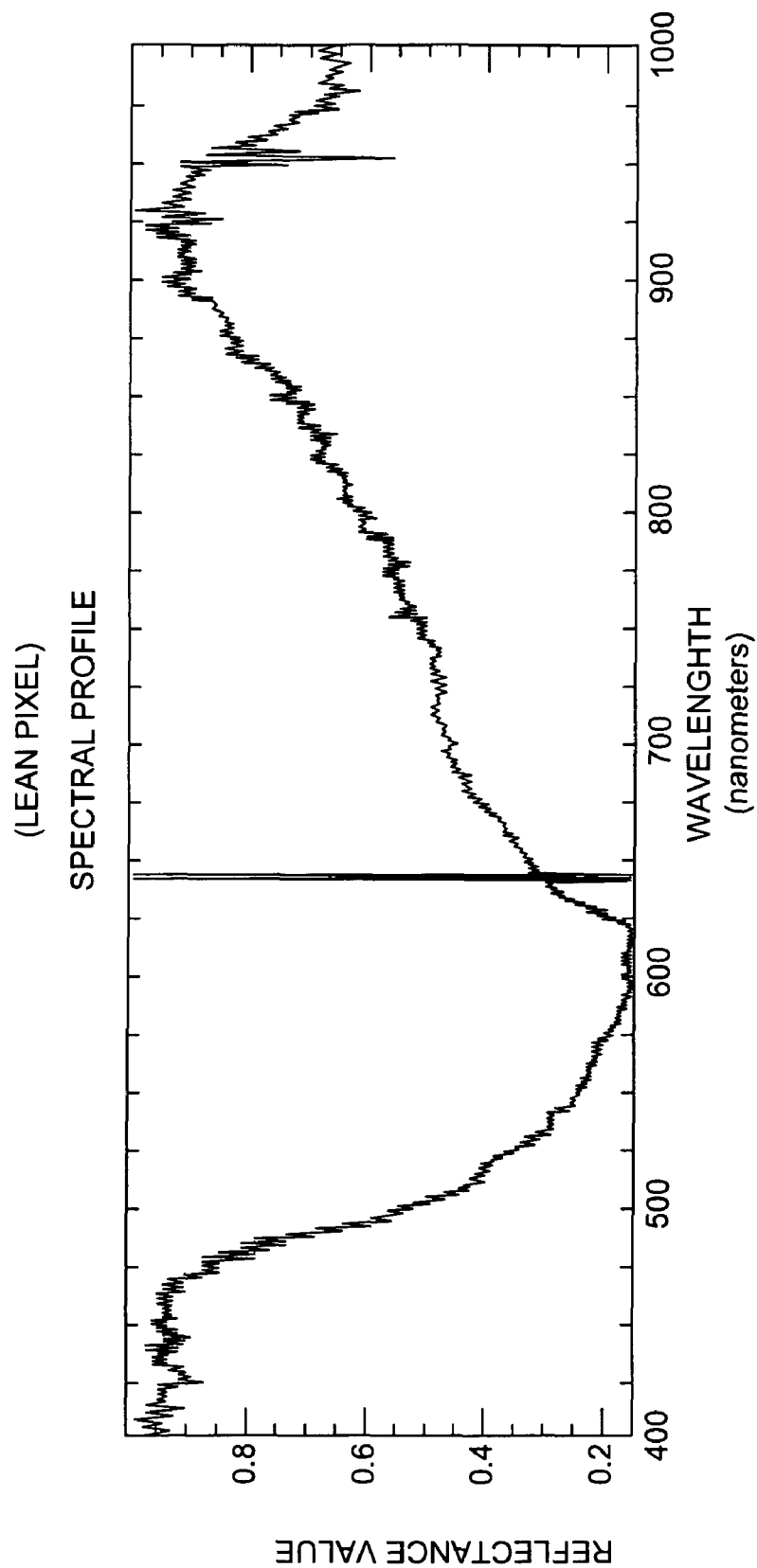
FIG. 5 illustrates an exemplary spectral profile of a lean pixel of a beef hyperspectral image according to an embodiment of the present invention.
Figure 6:
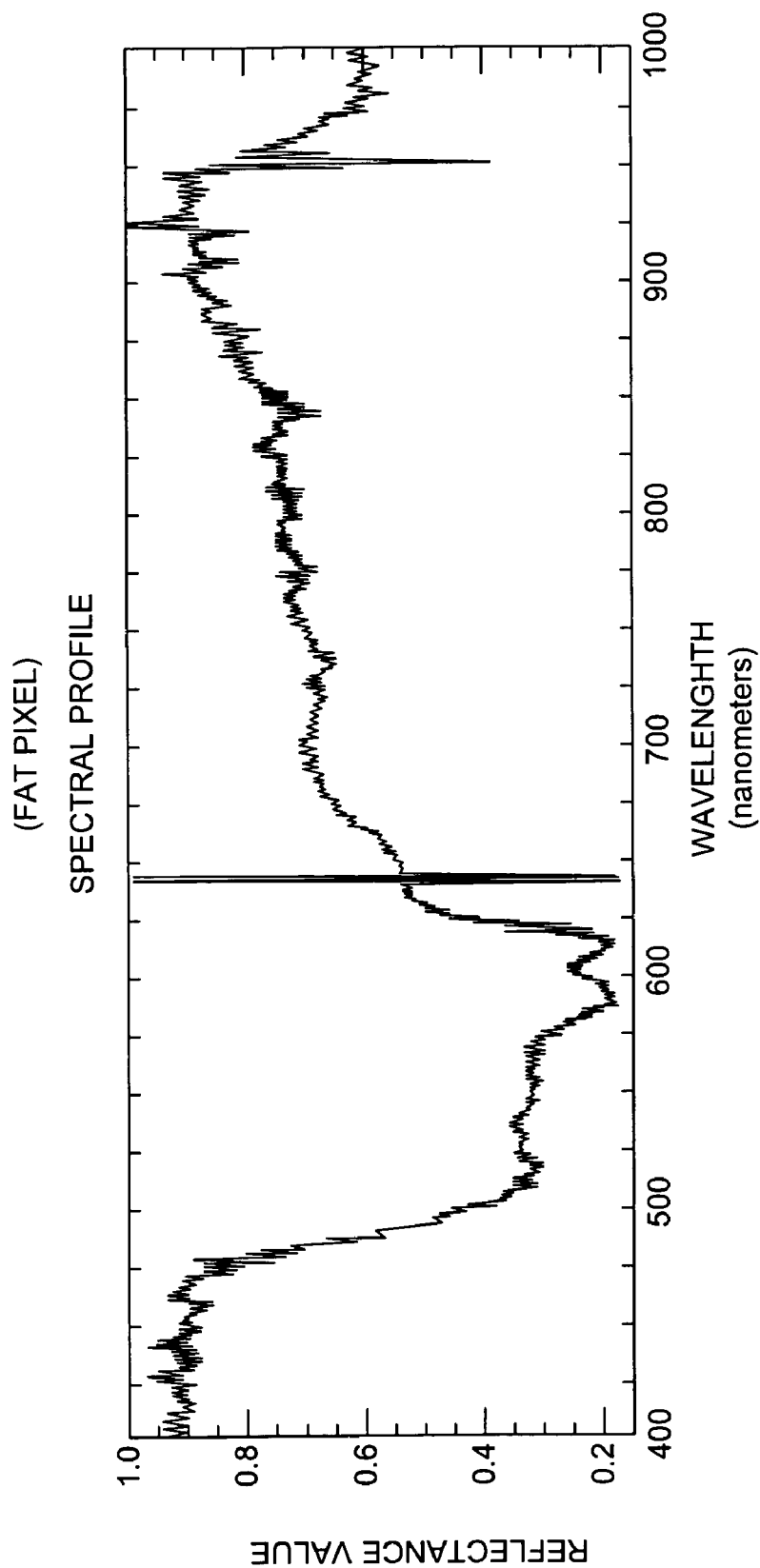
FIG. 6 illustrates an exemplary spectral profile of a fat pixel of a beef hyperspectral image according to an embodiment of the present invention.

Turning to FIG. 2, an exemplary method 200 for using hyperspectral imaging to determine material properties of an object is shown. At step 202, a hyperspectral image of at least a portion of an object is obtained. As will be readily appreciated by those skilled in the art, a hyperspectral image may include a plurality of pixels wherein each pixel includes a plurality of spectral bands. A spectral profile may be obtained from the hyperspectral image in order to illustrate the nature of the spectral image. For example, FIGS. 5 and 6 each illustrate an exemplary spectral profile obtained from a single pixel of a hyperspectral image. The exemplary spectral profile in FIG. 5 shows a spectral profile of a pixel corresponding to a lean portion of a cut of beef. The exemplary spectral profile in FIG. 6 shows a spectral profile of a pixel corresponding to a fat portion of a cut of beef. In some embodiments, a hyperspectral image may comprise hundreds of narrow spectral bands, which may be represented in a spectral profile.

In an embodiment of the invention, the hyperspectral image that is received at step 202 may be processed or unprocessed. As will be appreciated by those skilled in the art, an image may be processed in various ways to achieve a multitude of objectives. In one embodiment, for example, the hyperspectral image may be processed to eliminate variations due to temperature.

At step 204, a dimensionality reduction technique is performed to remove redundant information from the hyperspectral image, thus creating a simplified image. In one embodiment, principal component (PC) bands may be identified from the plurality of spectral bands that comprise the hyperspectral image. The PC bands may be identified by performing a principal component analysis to reduce the dimension of the data along the spectral axis. For example, in one embodiment, five PC bands may explain 90% of the variance of all the bands in the image.

In a further embodiment of the present invention, redundant information is removed by identifying partial least squares (PLS) bands of the hyperspectral image are identified by performing a partial least squares analysis. For example, in one embodiment, the method 200 may be used to analyze a fresh cut of beef to predict cooked-beef tenderness. Because lean and fat pixels have different spectral profiles, as illustrated in FIGS. 4-5, PLS may be performed separately on fat and lean pixels. In one embodiment, for example, an unsupervised K-means classification may be used to separate fat and lean pixels. The mean spectra of all fat pixels and mean spectra of all lean pixels may be determined. PLS analysis may be performed on these mean spectra, for example, by utilizing chemometric software. PLS may facilitate maximization of the variation of the mean spectra of lean pixels among samples. The number of eigenvectors may be determined to explain variance in spectra. Additionally, the loading vectors for lean pixels may be determined. Similarly, PLS may be performed separately for fat pixels and the corresponding loading vectors may be determined. In an embodiment, the loading vectors give the coefficients for linear combinations of reflections at various wave lengths that may be used to determine PLS scores.

When a new, simplified hyperspectral image is obtained, fat and lean pixels may be classified, in one embodiment, using an unsupervised K-means clustering for fat pixels. The fat PLS loading vectors may be used to determine PLS scores. Similarly for lean pixels, the lean PLS loading vectors may be used to determine PLS scores. For example, if there are five eigenvectors, then five PLS-score images may be obtained from the hyperspectral image. In various embodiments of the present invention, PLS images could contain more information about beef tenderness than PC images because the differences in the PLS for different samples may indicate a difference in tenderness.

With continued reference to FIG. 2, image-textural features are extracted from the simplified image at step 206. In one embodiment of the invention, image-textural features may be extracted by performing a co-occurrence matrix analysis. In various other embodiments, other forms of analysis may be used to extract various image-textural features from the simplified image such as, for example, wavelet analysis and analysis that utilizes Gabor filters. Image-textural features may include features such as, for example, mean, variance, homogeneity, contrast, dissimilarity, entropy, second moment, and correlation.

At step 208, image-textural features are correlated with material properties of the object. In one embodiment, the image-textural features may be inputted into a canonical discriminant algorithm that defines two canonical variables to represent, for example, three categories of tenderness (e.g. tender, intermediate, and tough). In various other embodiments, other forms of pattern recognition algorithms may be used to correlate extracted image-textural features with material properties of an object. Such pattern recognition algorithms can include, for example, regression, neural networks, and fuzzy modeling.

In a further embodiment, image-textural features that are outputted from a PLS analysis may be correlated with material properties of the object. For example, in one embodiment, the method 200 may be used to predict cooked-beef tenderness by analyzing a corresponding cut of fresh beef. In this example, a regression approach may be used to determine tenderness scores at each pixel using PLS scores. These values may then be integrated to determine, for example, a tenderness grade. This determination may be made using any number of various techniques. In one embodiment, an averaging scheme with thresholds for different classes may be used. In another embodiment, a nonlinear function may be defined to determine, for example, the tenderness score for the whole sample. In a further embodiment, discriminant analysis may be used to classify each pixel in an image according to material properties, such as, for example, "tender", "intermediate", or "tough". In an embodiment, the class with the largest number of pixels may be assigned for the whole sample, whereas in other embodiments, the sample may be classified in portions.

Figure 3:
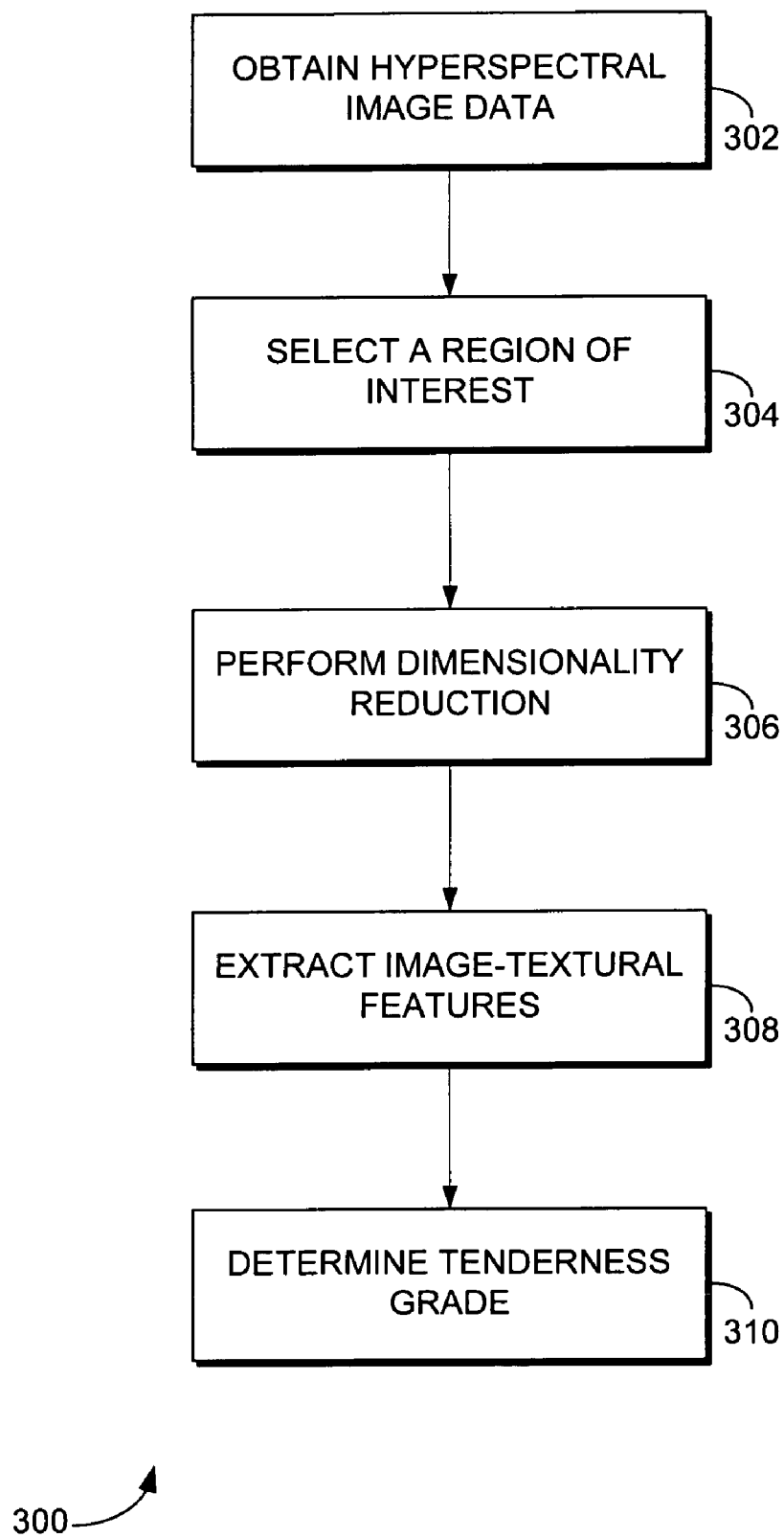
FIG. 3 is a flow diagram illustrating an exemplary method for predicting a cooked-beef tenderness grade corresponding to a fresh cut of beef by analyzing material properties of the fresh cut of beef using hyperspectral imaging according to an embodiment of the present invention.

Referring now to FIG. 3, an exemplary method 300 is shown for predicting a cooked-beef tenderness grade by analyzing material properties of a corresponding fresh cut of beef using hyperspectral imaging according to an embodiment of the present invention. At step 302, hyperspectral image data is obtained. The hyperspectral image data may include data corresponding to a hyperspectral image of at least a portion of a cut of beef. In an embodiment of the present invention, the hyperspectral image may include a plurality of lean pixels and a plurality of fat pixels.

At step 304, a region of interest is selected. In one embodiment, the region of interest may include a portion of the hyperspectral image data. In another embodiment, the region of interest may include the entire hyperspectral image. The region of interest may be selected based on any number of various criteria known in the art. For instance, in one embodiment, the region of interest may correspond to a location on a cut of beef that approximates the location for which material properties of a cut of beef have been estimated using some other procedure known in the art.

In one embodiment, for example, the region of interest may correspond to an approximate location at which a shearing procedure was performed. Such a shearing procedure, as will be appreciated by those skilled in the art, may provide slice shear force (SSF) values for various cuts of beef. In an embodiment, samples of beef may be classified into tenderness categories based on the SSF values. For example, in an embodiment, a cut of beef may be classified into three tenderness categories: tender (SSF=<21 kg), intermediate (21.1 kg<=SSF=<24.9 kg), and tough (SSF>=25 kg). In an embodiment, these categories may be used as references for tenderness classifications of data obtained according to various methods and algorithms described herein.

At step 306, the dimensionality of the spectral data is reduced. This may be achieved, for example, by removing redundant data such as by performing a PC or PLS analysis. In further embodiments, other known dimension reduction techniques may be utilized to simplify the image data corresponding to the region of interest. At step 308, one or more image-textural features are extracted. The image-textural features are analyzed at step 310 to determine a tenderness grade for the cut of beef. As discussed above, with reference to FIG. 2, various methods may be utilized in determining a tenderness grade.

Various embodiments of the present invention provide for systems and methods of using hyperspectral imaging to determine material properties of an object. In an embodiment of the present invention, the system and methods described herein may be used to determine various properties and classifications of properties for cuts of beef. In one embodiment, the present invention may be used to predict tenderness of beef.

In other embodiments, systems and methods as described herein may be utilized to analyze material properties of other meat products. In one embodiment, for example, embodiments of the present invention may be implemented to analyze material properties of pork. In further embodiments, the present invention may be implemented to analyze material properties of lamb. In still further embodiments, the present invention may be utilized to predict tenderness grades for meat products such as, for example, pork or lamb.

In various embodiments of the present invention, systems and methods as described herein may be used to detect tissue lesions in samples of tissue. In some embodiments, aspects of the present invention may be utilized to detect cancerous tissue within a tissue sample. In various embodiments, transmission spectroscopy may be used to detect abnormalities in a tissue sample. In further embodiments, scattering spectroscopy may be used to detect abnormalities in a tissue sample.

The present invention has been described in relation to particular embodiments, which are intended in all respects to be illustrative rather than restrictive. Alternative embodiments will become apparent to those skilled in the art to which the present invention pertains without departing from its scope.

From the foregoing, it will be seen that this invention is one well adapted to attain all the ends and objects set forth above, together with other advantages which are obvious and inherent to the system and method. It will be understood that certain features and sub-combinations are of utility and may be employed without reference to other features and sub-combinations. This is contemplated and within the scope of the claims.

The invention claimed is:

1. A method for determining material properties of an animal tissue, said method comprising:
   a. using an imaging component to obtain a hyperspectral image of at least a portion of said animal tissue, said hyperspectral image comprising data along the spectral axis consisting of hundreds of narrow spectral bands, said imaging component comprising a hyperspectral camera and a lighting system, said lighting system selected from the group consisting of a concentrated lighting system and a diffuse lighting system; wherein said hyperspectral camera is configured to perform a technique of imaging selected from the group consisting of reflectance, transmission, scattering, fluorescence, and x-ray transmission, and wherein said hyperspectral camera is configurable to collect images in the wavelength range of 200 nm to 12,000 nm, whereby said hyperspectral camera is actuated and a hyperspectral image of said portion of said animal tissue is obtained; and
   b. using an analysis component comprising a system having computer programming to analyze said hundreds of spectral bands of said hyperspectral image to generate material properties data that describes material properties of said animal tissue, said system employing a reduction component to remove redundant information in said data contained in said hyperspectral image, whereby a simplified image is created, said system further employing an extraction component to extract image-textural features from said simplified image, thereby creating extracted image-textural feature data, said system further employing a recognition component for using pattern recognition algorithms to relate said extracted image-textural feature data to said material properties associated with said animal tissue, and said system further comprising an output component for outputting said materials property data, wherein said animal tissue is a meat product, wherein said meat product is a fresh cut of beef, and wherein said material property is a prediction of cooked-beef tenderness, and wherein said beef is classifiable into a category based on said material property prediction of cooked-beef tenderness.

2. The method of claim 1, wherein said removing of redundant information comprises performing at least one analysis selected from the group consisting of principal component analysis and partial least squares regression analysis to reduce the dimension of the data along the spectral axis.

3. The method of claim 1, wherein said extracting of image-textural features is performed by a technique selected from a co-occurrence matrix analysis, a wavelet analysis, an analysis that utilizes Gabor filters, and combinations thereof.

4. The method of claim 1, wherein a region-of-interest from the hyperspectral image is selected to correspond to an approximate location on said cut of beef at which a shearing procedure was performed.

5. The method of claim 4, wherein a region-of-interest is selected from a lean region of said meat product and a fat region of said meat product.

6. The method of claim 5, wherein a fat mean spectra of all fat pixels and a lean mean spectra of all lean pixels is determined by said analysis component from said hyperspectral image, and thereafter said analysis component performs partial least squares regression analysis on each of said fat and lean mean spectra.

7. The method of claim 6, wherein said analysis component determines eigenvectors to explain variance in spectra.

8. The method of claim 6, wherein said analysis component determines loading vectors for lean pixels and loading vectors for fat pixels.

9. The method of claim 8, wherein the loading vectors give the coefficients for linear combinations of reflections at various wavelengths that may be used to determine tenderness scores.

10. The method of claim 9, wherein said tenderness scores at each pixel are integrated or aggregated to determine a single tenderness category per image or sample.

11. The method of claim 9, wherein said tenderness scores are analyzed by said analysis component by implementing programming selected from the group consisting of: an averaging scheme with thresholds for different categories, a non-linear function defined to determine a tenderness category for the entire sample, and discriminant analysis used to classify each pixel in an image according to material properties.

12. The method of claim 6, wherein said analysis component implements a regression approach to determine tenderness scores at each pixel using partial least squares regression analysis.

13. The method of claim 1, wherein said analysis component processes said hyperspectral image to obtain a spectral profile from a single pixel of said hyperspectral image.

14. The method of claim 13, wherein said spectral profile of a pixel corresponds to a lean portion of a cut of beef.

15. The method of claim 13, wherein said spectral profile of a pixel corresponds to a fat portion of a cut of beef.

16. The method of claim 1, wherein said pattern recognition algorithm is selected from the group consisting of regression, discriminant analysis, neural networks, and fuzzy modeling, whereby said textural features are related to properties associated with said animal tissue.

* * * * *

UNITED STATES PATENT AND TRADEMARK OFFICE
CERTIFICATE OF CORRECTION

PATENT NO. : 8,280,144 B2  
APPLICATION NO. : 12/035080  
DATED : October 2, 2012  
INVENTOR(S) : Subbiah et al.

Page 1 of 1

It is certified that error appears in the above-identified patent and that said Letters Patent is hereby corrected as shown below:

In the Specification

Col. 2, line 49, replace "related to aging is not" with -- related to aging, is not --
Col. 2, line 51, replace "In NIR analysis light reflected" with -- In NIR analysis, light reflected --
Col. 2, line 56, replace "is not considered" with -- is not considered. --
Col. 3, line 22, replace "which may correspond to 8,000 to 12,000 nm." with -- which may correspond to the wavelength range of 8,000 to 12,000 nm. --
Col. 3, line 29, replace "wavelength ranges such as" with -- wavelength ranges, such as --
Col. 3, line 41, replace "sensors according to the embodiments discussed above others" with -- sensors, according to the embodiments discussed above, others --
Col. 3, line 48, replace "Model IPX-2M30 camera made by" with -- Model IPX-2M30 camera, made by --
Col. 3, line 55, replace "the linear slide Model: MN10-0300," with -- the linear slide Model MN10-0300, --
Col. 3, line 67, replace "hyperpectral" with -- hyperspectral --
Col. 4, line 13, replace "fluorescence imaging or broad-band" with -- fluorescence imaging, or broad-band --
Col. 4, line 37, replace "example Munsell" with -- example, Munsell --
Col. 4, lines 62-63, replace "algorithms etc.," with -- algorithms, etc., --
Col. 5, line 3, replace "redundant information such as" with -- redundant information, such as --
Col. 5, line 47, replace "labeling component 112" with -- labeling component 120 --
Col. 5, line 54, replace "plurality of pixels wherein" with -- plurality of pixels, wherein --
Col. 6, line 18, replace "hyperspectral image are identified by" with -- hyperspectral image, which are identified by --
Col. 7, line 31, replace "image data is obtained." with -- image data are obtained. --

Signed and Sealed this  
Eighteenth Day of March, 2014

Michelle K. Lee  
*Deputy Director of the United States Patent and Trademark Office*